United States Patent [19]

Wirtz

[11] Patent Number: 5,489,272
[45] Date of Patent: Feb. 6, 1996

[54] INJECTION SYRINGE

[75] Inventor: Matthias Wirtz, Moers, Germany

[73] Assignee: Medi Plus Tec Medizinisch-Technische Handelgesellschaft mbH, Moers, Germany

[21] Appl. No.: 324,586

[22] Filed: Oct. 18, 1994

[30] Foreign Application Priority Data

Oct. 18, 1993 [DE] Germany ............................ 9315861 U

[51] Int. Cl.⁶ ..................................................... A61M 5/00
[52] U.S. Cl. ............................ 604/110; 604/220; 604/195
[58] Field of Search ............................... 604/110, 187, 604/218, 220, 228, 195, 263

[56] References Cited

U.S. PATENT DOCUMENTS

| | | | |
|---|---|---|---|
| 4,888,002 | 12/1989 | Braginetz et al. | 604/220 X |
| 4,919,652 | 4/1990 | Alter et al. | 604/110 |
| 5,106,372 | 4/1992 | Ranford | 604/110 |
| 5,246,423 | 9/1993 | Farkas | 604/218 X |
| 5,380,285 | 1/1995 | Jenson | 604/110 |

*Primary Examiner*—John D. Yasko
*Attorney, Agent, or Firm*—Felfe & Lynch

[57] ABSTRACT

A tubular barrel having an inner surface with threads at a front end thereof receives a chuck having corresponding threads for engaging the chuck to the barrel, the chuck having additional threads in an opposite sense for engaging a needle hub thereto. A piston received slidably in the barrel engages the rear of the chuck and is fixed against rotation relative to the hub, whereby a piston stem protruding from the rear of the barrel can be used to engage the chuck to the front end of said barrel. Cams provided on the inside surface cooperate with flexible cam followers on the chuck to make disengagement of the chuck from the barrel more difficult than engagement. A circumferential rib provided on the inside surface at the rear of the barrel impedes withdrawal of the piston, the stem being frangible to prevent the reuse.

11 Claims, 6 Drawing Sheets

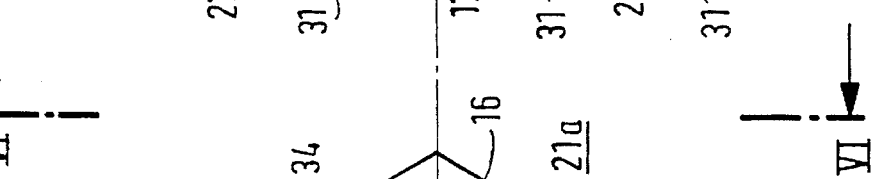
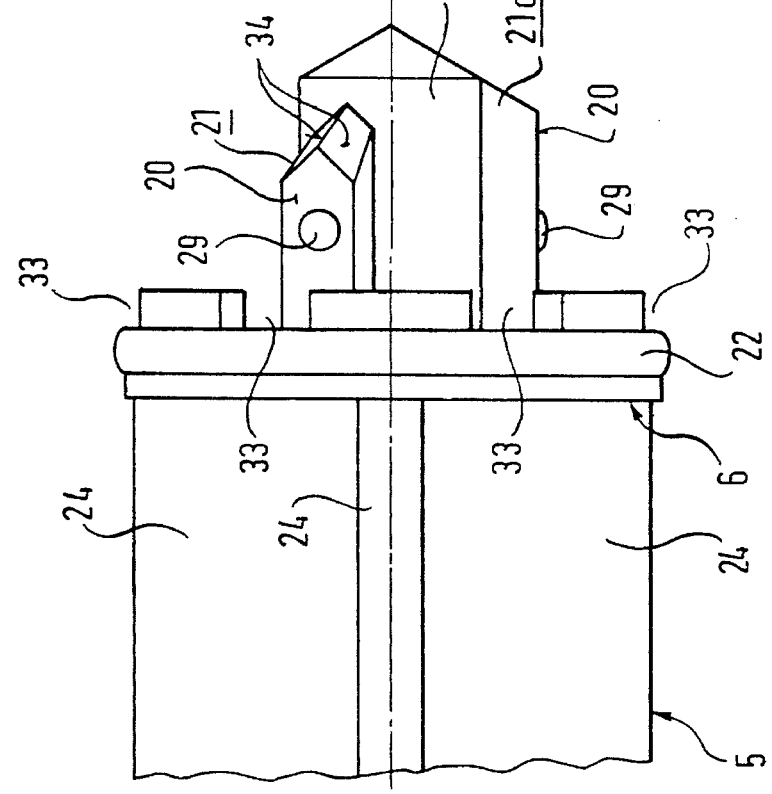

5,489,272

INJECTION SYRINGE

BACKGROUND OF THE INVENTION

The invention relates to an injection syringe with a barrel on whose one end a chuck surmounted by an injection needle can be attached, having a piston displaceable in the barrel, on which a piston rod protruding from the other end of the barrel and provided at its extremity with an operating handle is provided. A system on the chuck automatically locks the piston when the latter is advanced by a given amount in the direction of the needle to prevent withdrawal of the piston, and the chuck can be joined to the barrel by a rotational connection to be released by turning it in and in some cases by axial displacement of the chuck in the barrel. Antirotational members are on the chuck and piston, which, when the piston is pushed forward toward the chuck, interact to lock the piston on the chuck, and by the rotation of the operating member permit a release of the rotational connection and then a withdrawal of the piston, chuck and needle into the cylinder over their entire length. The antirotational members are projections at angular distances from one another and can be brought by axial displacement of the piston into mutual, meshing engagement.

An injection syringe of this kind is disclosed in European Patent Application, publication No. 402,908. In this injection syringe the chuck can relatively easily be released from its rotational connection to the barrel.

Often medicaments have to be drawn into injection syringes by means of a needle which has to pierce a closure, say of rubber or plastic, before it can penetrate into the vessel containing the medicament. For this purpose a comparatively strong needle has to be used, which usually has a comparatively large inside diameter. The result is that components of the pierced closure, such as rubber or plastic particles, can be drawn into the injection syringe. In no way are such particles to be injected. For this reason the needle serving to draw in the medicament must be replaced by a needle with a smaller inside diameter. When such a replacement is made, if a syringe of the kind described above is used, it is possible that the chuck might loosen a little and allow medicament to escape between the chuck and the barrel.

SUMMARY OF THE INVENTION

To prevent this, the injection syringe is characterized by the fact that locking means are provided between the inside circumference of the cylinder and the outside circumference of the chuck which will permit a comparatively easy turning in of the rotational coupling between the chuck and the barrel and a comparatively difficult turning out of the rotational coupling.

Design-wise it is especially simple if the locking means are formed by asymmetrical cams and resiliently yielding cam followers are formed over these asymmetrical cams. According to an easy-to-manufacture embodiment, the cams are in the form of ramps and the cam followers the form of elastic fingers. In that case the cams are preferably on the barrel and the cam followers on the chuck. An especially effective embodiment is characterized by the fact that the cams are on the inside surface of the barrel and the cam followers on the end of the chuck facing the piston. Since cam followers in the form of fingers must be able to yield, recesses are preferably provided in the periphery of a base on the piston to accommodate the cam followers.

To assure that the needle cannot be pushed back out of the barrel, it is often prescribed that the piston has to be broken off after the retraction of the needle. To achieve this, the injection needle is preferably characterized by the fact that points are created by injection molding around the circumference on the keys of the piston that face the chuck by means of bevels sloping toward one another. Independently of the features described above, this feature has an inventional significance of its own.

One especially simple means for locating the piston on the chuck is cooooperating projections which prevent rotation. Between the radially outwardly facing surfaces of the projections and/or of the spaces between the projections, on the one hand, and the radially inward facing boundary surfaces of the spaces between the projections and/or the projections on the chuck, on the other hand, latching means are provided which can be released from one another. This feature too is of independent significance.

BRIEF DESCRIPTION OF THE DRAWING

FIG. 4 shows the front end of the piston enlarged, FIG. 5 shows the back end of the chuck, likewise enlarged.

DETAILED DESCRIPTION OF THE PREFERRED EMBODIMENTS

Figure 1:
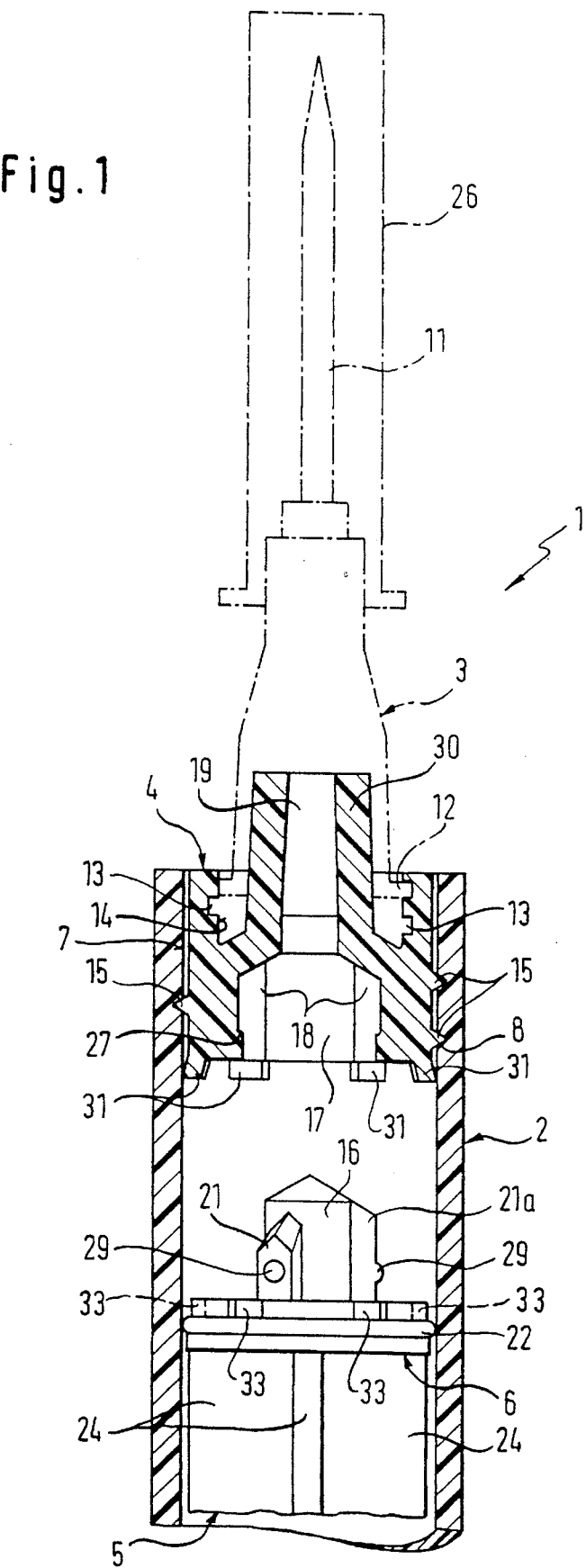
FIG. 1 is a longitudinal section through the front part of an injection syringe according to a first embodiment.
Figure 2:
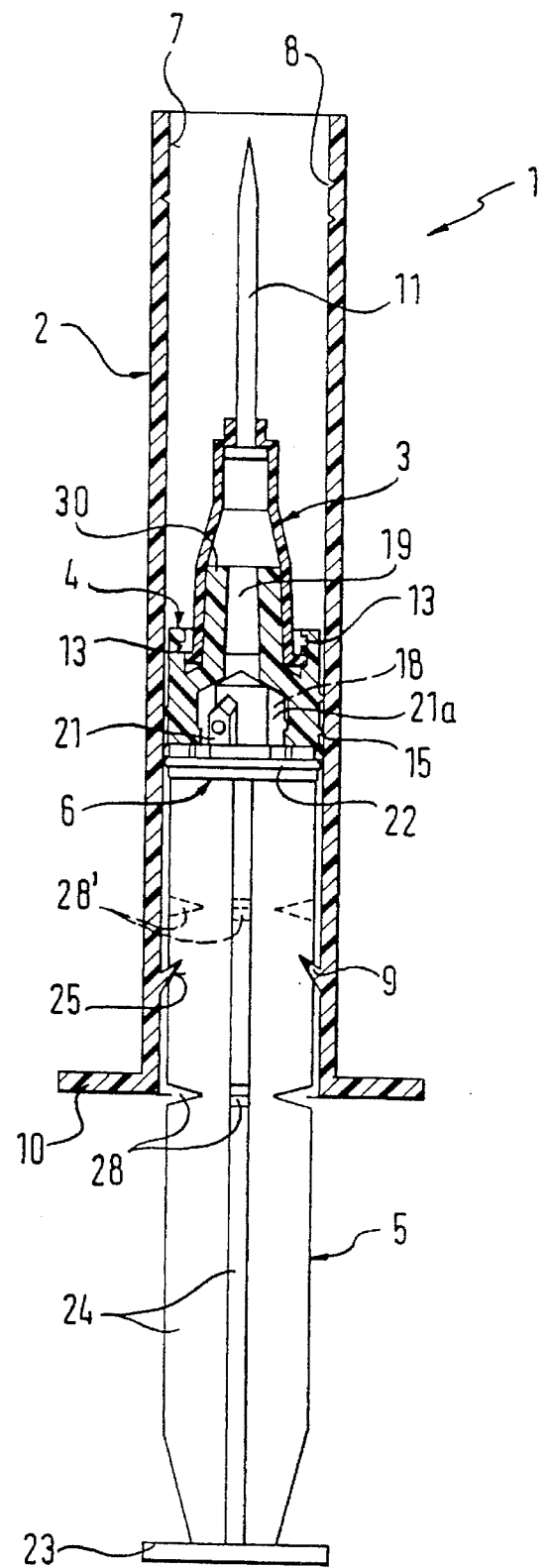
FIG. 2 is a longitudinal section through the injection syringe of FIG. 1, with a piston retracted into the barrel together with the chuck and the needle and locked in the cylinder.

The injection syringe 1 has a barrel 2 of constant diameter, in which a piston stem 5 is guided for displacement, a needle hub 3 for an injection needle 11, a needle chuck 4 for the needle hub 3, and a piston 6 which is integral with the piston stem 5. The barrel 2 is provided with a first left-hand thread section 8 into which a second left-hand thread section 15 on the needle chuck 4 is screwed by counter-clockwise rotation. Nose-shaped locking projections 9 formed into the rear portion of the barrel 2 can be snapped into the nose-shaped locking recesses 25 in guiding wings 24 of cruciform cross section on the piston stem 5. At the rear end of the cylinder 2 are external finger holds 10 for a round operating button 23 on the free end of the piston stem 5, by means of which the piston stem 5 can be rotated and pushed.

The needle hub 3 is releasably fastened in the front end of the chuck 4. For this purpose a flange 12 is formed on the outside of the needle hub 3, and into an inner wall 14 of the chuck 4 there is formed a right-hand threaded section 13 into which the flange 12 of the needle hub 3 can be screwed clockwise. Alternatively, a non-rotating plug-type binding between the needle hub 3 and the inner wall 14 of the needle chuck 4 may be provided.

The threaded section 15 screwed into the threaded section 8 of barrel 2 is formed in the outer periphery of the rear middle portion of the chuck.

The chuck 4 is provided at the back with a cavity 17. Antirotational members 18 project radially inward from the inner wall of the chuck 4 around the back of the cavity 17. A passage 19 runs through the forward center part of the chuck 4 and through it the fluid that is to be injected reaches the needle 11.

Antirotational members 21, 21a for meshing engagement with the antirotational members 18 of the chuck 4 project radially from a front hub 16 of piston 6. One of these antirotational members 21a is longer toward the chuck 4 than the other members 21. The antirotational members 21 on piston 6 are sharpened by means of bevels sloping toward one another in the direction of the chuck 4. The periphery of piston 6 is provided with a rounded edge 22 in close contact with the inner wall 7 of the barrel 2. On the radially outwardly facing sides 20 of the antirotational members 21 are nubs 29; to lock the piston 6 to the chuck 4 these are forced behind internal shoulders 27 between the antirotational members 18 at the entrance to the cavity 17.

Figure 8:
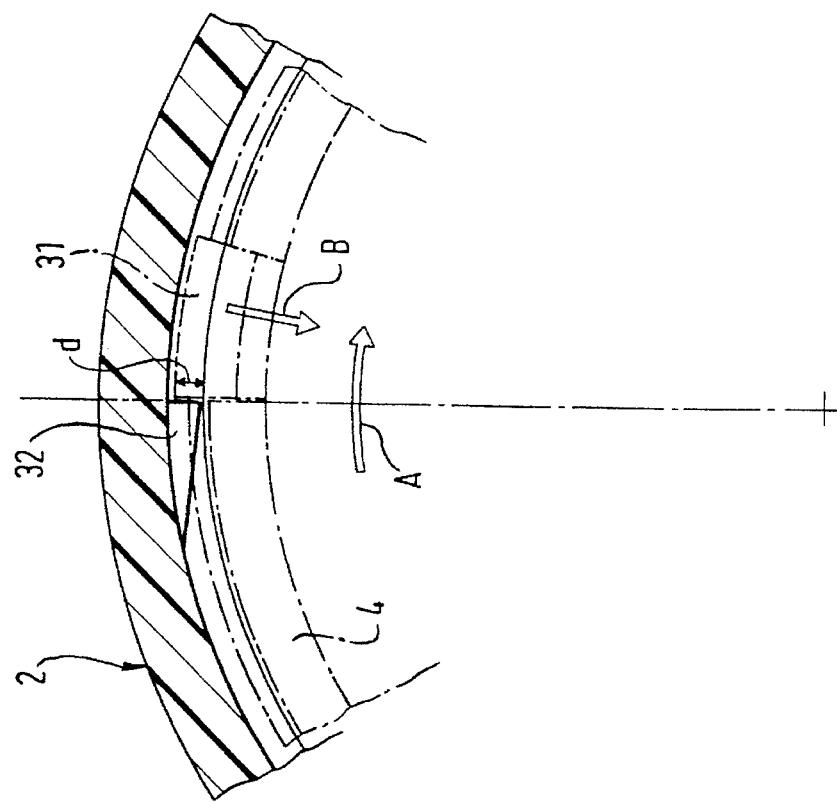
FIG. 8 shows the interaction of the locking means between chuck and barrel as seen in direction VIII—VIII in FIG. 7.
Figure 7:
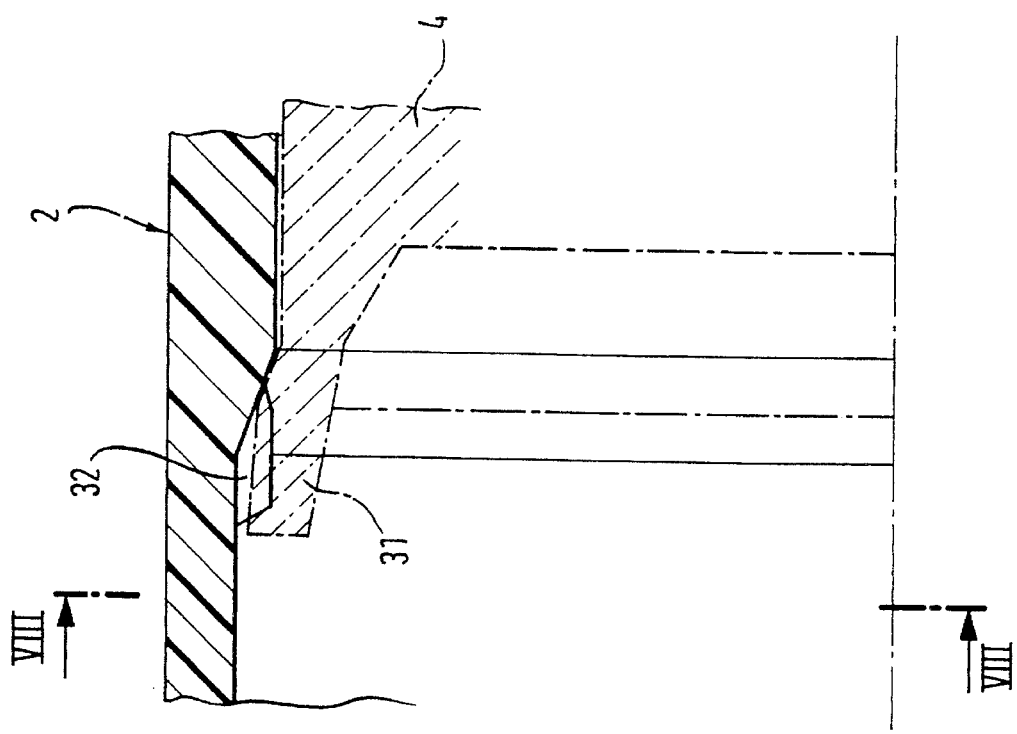
FIG. 7 shows the interaction of the locking means between chuck and barrel in an axial section.

On the inside of the barrel 2 are ramps 32 (FIG. 7), and on the end of the chuck facing the piston 6 are flexible fingers 31. When the chuck 4 is screwed into the barrel 2 (directional arrow A in FIG. 8) when fingers slide up the ramps 32 while flexing in arrow direction B (FIG. 8), and, when they have passed beyond the ramps 32 they snap radially outward again. If the chuck 4 is to be unscrewed from the barrel 2 (opposite the arrow direction A), its fingers 31 collide with the ramps 32 and impede unscrewing to a limited extent. In an actual embodiment, the distance d in FIG. 8 is only 0.2–0.3 mm. The configuration can be made such that, when the chuck 4 is unscrewed from the bar barrel 2, the fingers 31 are pinched off and destroyed, contributing to the one-time use of the injection syringe.

The guiding wings 24 of cruciform configuration and the piston stem 5 are cemented to the round operating button 23. The nose-shaped locking recesses 25 in the piston 6 are yieldingly engaged by the nose-shaped locking projections 9 in barrel 2 when the piston 6 is drawn rearwardly and they prevent complete withdrawal of the piston stem 5 from the barrel 2. However, the piston stem 5 can then be easily broken off by means of notches 28 in the guiding wings, which in this state are outside of the barrel 2.

As an alternative means for preventing withdrawal of the piston 5 from barrel 2, the inner surface 7 of the barrel 2 can be provided with a circumferential rib near the rear end of the barrel. Such a rib would impede passage of rounded edge 22 on the piston. In this case, the projections 9 and recesses 25 would be deleted, and the piston stem 5 would be made frangible by notches 28'.

Before use, in this example the chuck 4 is screwed with the hub 3 contrarily to the threaded connection between the chuck 4 and the barrel 2. Then the fingers 31 enter into the indentations 33, and pass over the ramps 32, until the state represented in FIG. 8 is reached. Then a needle cover 26 indicated in broken lines in FIG. 1 is removed.

Figure 3:
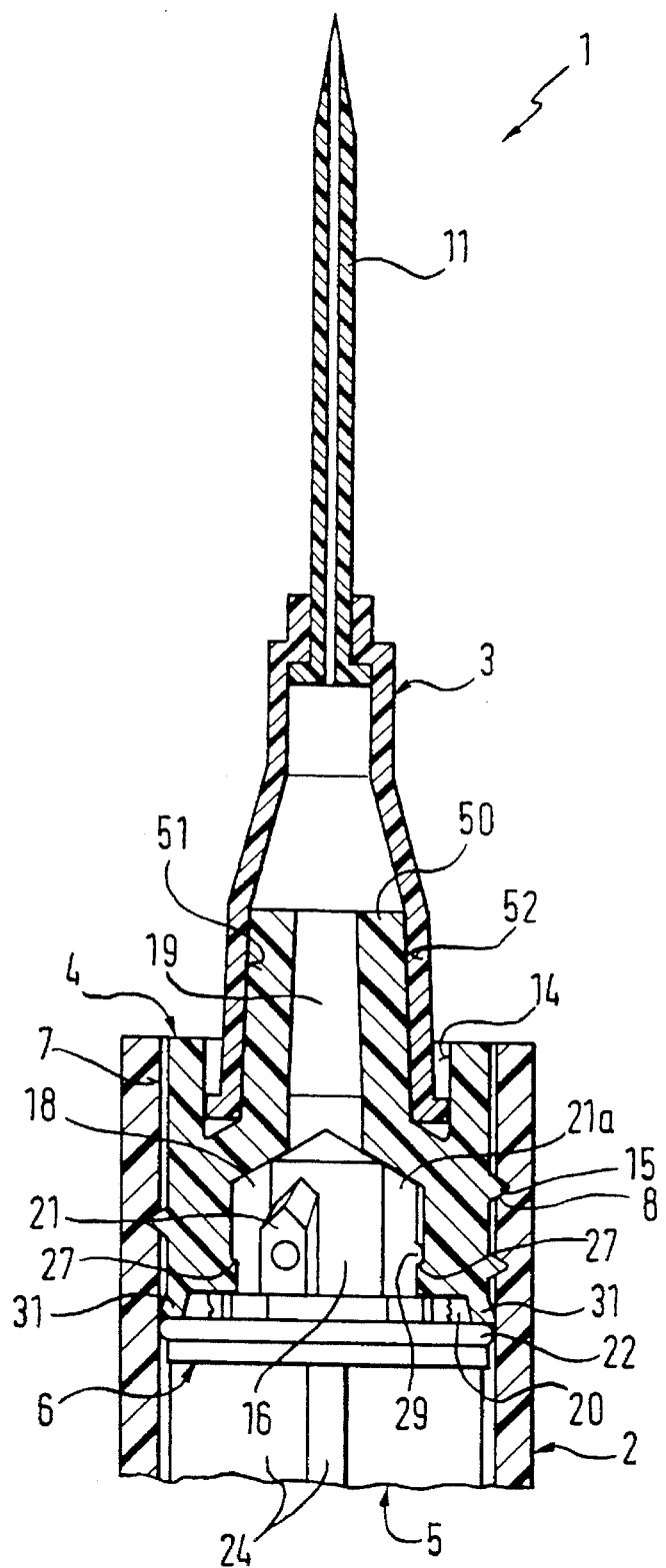
FIG. 3 is a longitudinal section through the front part of an injection syringe according to a second embodiment with a piston locked in the chuck.
Figure 6:
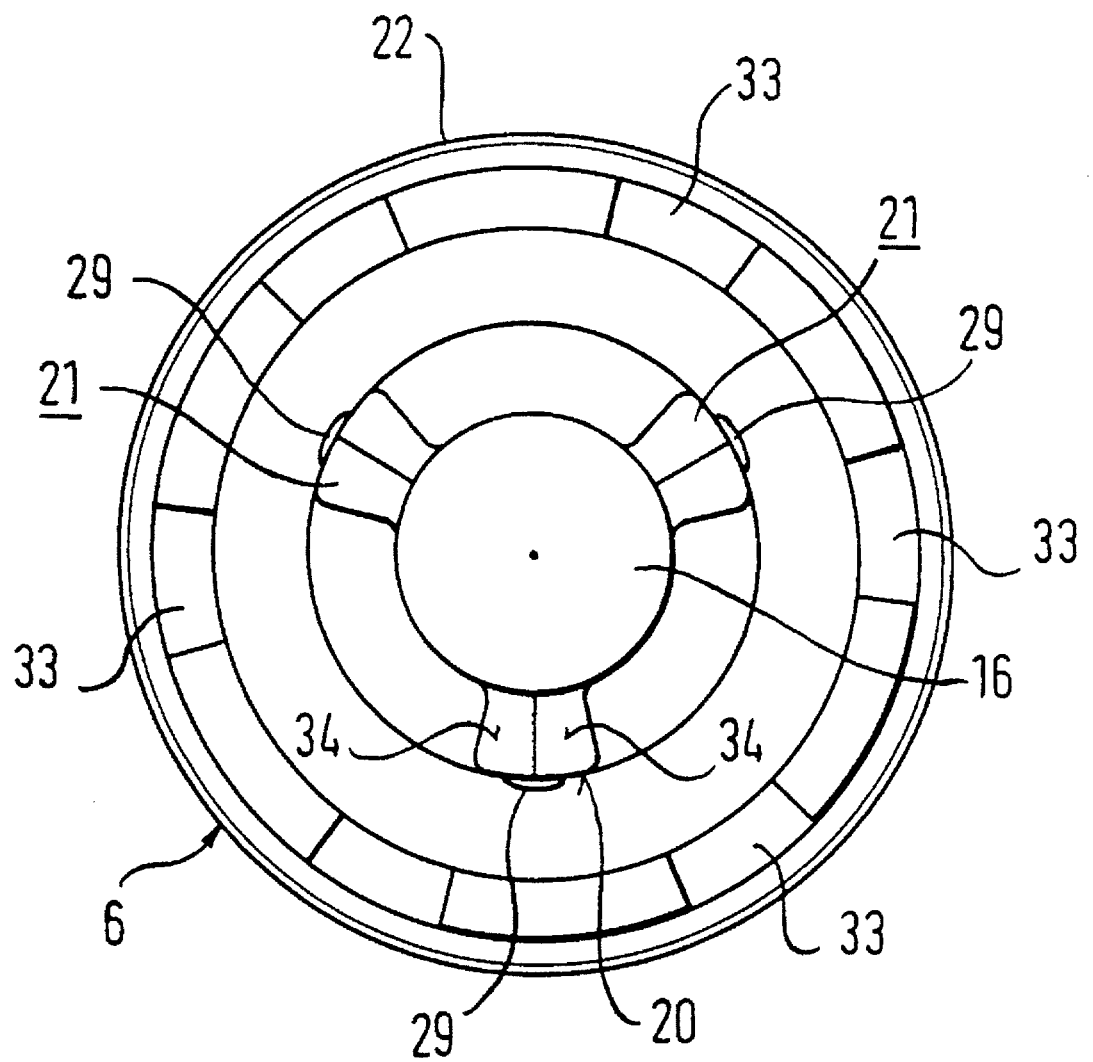
FIG. 6 is a view corresponding to VI—VI in FIG. 4.

FIG. 3 shows a second embodiment which differs from the first embodiment in having no internal threaded section 13 in an inner wall 14 of the chuck 4. Instead, a taper with external flats 51 is formed on the chuck, and onto these flats the needle hub 3 bearing mating flats 52 is to be drawn tightly and non-rotably.

The handling and operation of the injection syringes 1 according to the first embodiment will now be described.

To screw the chuck 4 to the barrel 2, the chuck 4 is inserted into the back end of the barrel 2, then pushed forward and given about one-quarter to one full rotation counterclockwise until the threaded section 15 on the chuck 4 has engaged the threaded section 8 on the inner wall of barrel 2. Then the flange 12 on the needle hub 3 is screwed clockwise onto the threaded section 13 of the chuck 4. The direction of rotation between the injection needle 11 and the chuck 4 is thus opposite that of the screw threads between the barrel 2 and the chuck 4.

After the needle hub 3 is inserted and after the needle cap 26 covering the needle 11 as indicated by the broken line in FIG. 1 has been removed, the needle 11 is used to pierce a plastic cap and then, after a needle replacement, inserted into a body, and then the piston 6 is pushed forward by means of the piston stem 5.

After the injection has been performed, the needle 11 is withdrawn from the body and the piston stem 5 is pushed forward by means of the operating button 23, until the antirotational members 21 on the front hub 16 of the piston 6 engage meshingly between the antirotational members 18 on check 4, and the nubs 29 have been forced behind the internal shoulders 4. The piston 6 is then firmly attached to the chuck 4.

If the piston 6 is then rotated, the antirotational members 18 pass into the cavity 17 of the chuck 4 into contact with the antirotational members 21 on the hub 16 of the piston 6. By further rotating the piston 6 by about one-quarter to a full rotation clockwise, the screw connection between the threaded section 8 in barrel 2 and the threaded section 15 on the chuck 4 is disengaged, as is the hold of the fingers 31 on the back of the ramps 32.

Then the piston 6 is pulled back until the nose-shaped locking projection 9 on the inner wall 7 of the barrel 2 snaps into the nose-shaped locking recesses 25 in the cruciform guiding wings 24, and is broken off. Then any displacement of the needle hub 3, needle chuck 4 and piston 6 is impossible. The needle 11 is then entirely inside of the barrel 2, so that any infection thereby is prevented.

The handling and the manner of operation of the injection needle 11 in accordance with the second embodiment are similar except for the plug-in junction between the needle hub 3 and the projection 30 on the chuck 4.

I claim:

1. Injection syringe comprising a tubular barrel having a first end, a second end, a cylindrical inner surface extending between said ends, and first thread means on said inner surface adjacent said first end, a chuck received slidably in said tubular barrel and having second thread means rotationally engagable with said first thread means, locking means between said inner surface of said tubular barrel and said chuck, said locking means being effective to make disengagement of said second thread means from said first thread means more difficult than engagement of said second thread means on said chuck to said first thread means, piston means comprising a piston received slidably in said tubular barrel and a piston stem protruding from said second end of said tubular barrel, and antirotation means for engaging said piston to said chuck so that said piston cannot be rotated relative to said chuck.

2. Injection syringe as in claim 1 wherein said locking means comprises asymmetrical cams on one of said barrel and said chuck, and elastically yielding cam followers on the other of said barrel and said chuck.

3. Injection syringe as in claim 2 wherein said cams are in the form of ramps and said cam followers are in the form of flexible fingers.

4. Injection syringe as in claim 2 wherein said cams are formed on said inside surface of said barrel and said cam followers are formed on said chuck.

5. Injection syringe as in claim 4 wherein said cam followers extend toward said piston, said piston being provided with recesses which accommodate the cam followers.

6. Injection syringe as in claim 1 wherein said antirotation means comprises radially extending projections on said piston and on said chuck, said projections on said piston being received between said projections on said chuck by moving said piston axially toward said chuck.

7. Injection syringe as in claim 6 wherein said projections on said piston extend radially outward, said chuck being formed with a recess in which said projections on said chuck extend radially inward.

8. Injection syringe as in claim 6 wherein said projections on said piston are provided with bevelled points facing said chuck.

9. Injection syringe as in claim 6 wherein one of said projections on said piston is longer toward the chuck than the other projections on the piston.

10. Injection syringe as in claim 6 wherein one of said projections on said piston and said projections on said chuck are provided with shoulder means, and the other of said projections on said piston and said projections on said chuck are provided with detent means, said detent means cooperating with said shoulder means so that disengagement of said piston from said chuck is more difficult than engagement of said piston to said chuck.

11. Injection syringe as in claim 1 wherein said antirotation means comprises releasable locking means effective between said piston and said chuck.

* * * * *